United States Patent [19]

Mattila

[11] 4,030,491

[45] June 21, 1977

[54] NASAL FILTER

[76] Inventor: Alvin Mattila, 2 Beaver St., San Francisco, Calif. 94114

[22] Filed: Oct. 31, 1975

[21] Appl. No.: 627,517

[52] U.S. Cl. .......................................... 128/140 N
[51] Int. Cl.[2] ...................................... A61M 15/08
[58] Field of Search ............ 128/140 N, 140 R, 206

[56] References Cited

UNITED STATES PATENTS 2,264,153 11/1941 Rowe ............................ 128/140 N
3,802,426 4/1974 Sakamoto ...................... 128/140 N

*Primary Examiner*—Robert W. Michell
*Assistant Examiner*—Henry J. Recla

[57] ABSTRACT

A filter that is adapted to be placed in the nostril of the nose includes a pair of containers, each having an open side and an opposite perforated side. The containers are formed by a flexible bridge. The open end of each container is closed by a perforated cover. A porous filter material is removably disposed in each container.

5 Claims, 4 Drawing Figures

NASAL FILTER

BACKGROUND OF THE INVENTION

This invention relates to a nasal filter. More particularly to a filter that has substantially the same shape as the opening of the nostrils thereby increasing effectiveness.

The prior art teaches a variety of insertable nasal filters, for example, those disclosed in U.S. Pat. Nos. 2,426,161; 2,433,565; 2,526,586; 2,535,155; 2,674,245; 2,890,695; 3,463,149; 3,747,597; and others. The foregoing are deficient, however, for one or more of the following reasons; they do not provide for a secure well fit; they contain extraneous connections, connections that could be painful; and they are not readily replaceable.

SUMMARY OF THE INVENTION

It is accordingly an object of the instant invention to provide for an approved nasal filter.

It is another object to provide for the same relatively little cost thereby making it generally available.

These and other objects of the invention will become more apparent from the following detailed disclosure and claims and by reference to the accompanying drawings, in which;

Figure 1:
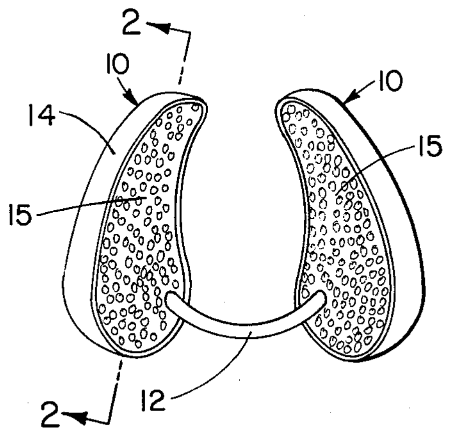
FIG. 1 is a front elevational view.
Figure 2:
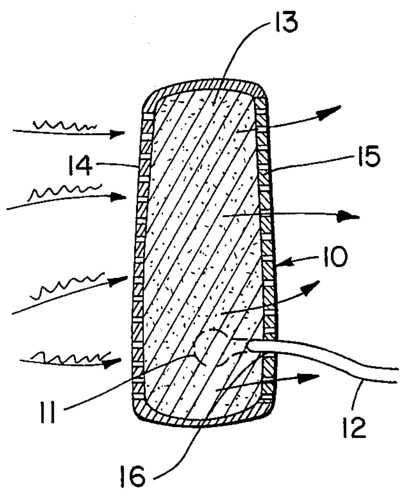
FIG. 2 is a sectional view of one filter container.
Figure 3:
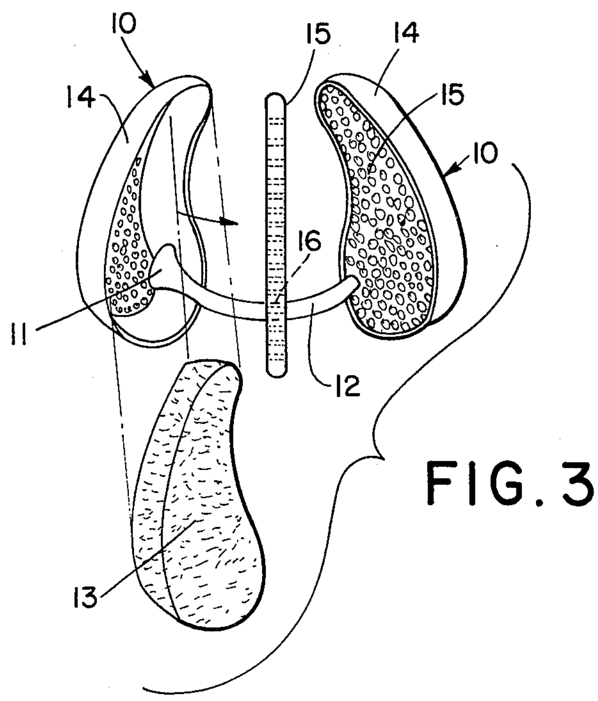
FIG. 3 is a perspective view of one assembled container and one disassembled container.
Figure 4:
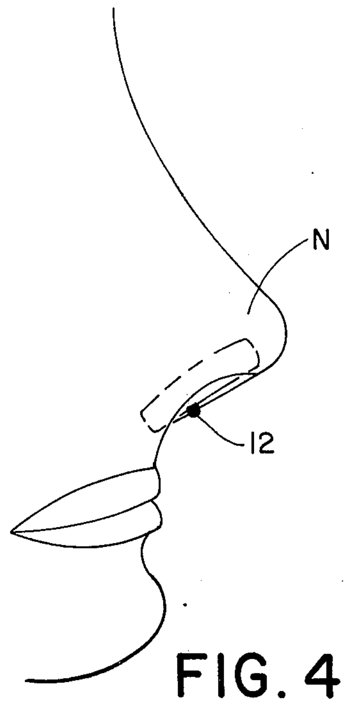
FIG. 4 is a perspective view of nasal filter in use.

Broadly speaking, the instant invention includes the provision of a nasal filter device adapted to be inserted into the nostrils of the nose, comprising a pair of walled containers each having one open side and an opposite perforated side, each open side facing inwardly, the bridge means having enlarged distal end portions extending through said open sides and joining the containers in any conventional manner, perforated covers for the containers and having apertures through which the bridge means slides to adapt the covers to slide towards each other on the means, porous filter means disposed in the containers, the filters being impregnated with a quantity of substantially liquid material, the containers having substantially the shape of the nostril.

DETAILED DISCLOSURE

Referring more particularly to the drawings, therein shown a pair of nasal filters 10 that from a nasal filter device. The filters 10 are connected by suitable means 12 such as wire or plastic clip that is non-allergenic. The means 12 is preferably arcuate shaped so as to fit under the septum of the nose N between the nostrils. Each end 11 of the means 12 will be preferably be enlarged such as bulb shaped and retain the filter 10 thereon in any conventional manner. The filter 10 contains a porous filter means 13 of a porous, perforate, lightweight, non-allergenic substance, such as wool, cotton, non-woven or the like and be easily replaceable. Each filter 18 also includes a container or housing 14 which has an open side through which the distal ends of bridging means 12 extends. Filter element 13 can be inserted into the removed containers 14 through the open side. Each container also has perforated cover 15 which defines an aperture through which bridging means 12 extends; replacement being effected by sliding the cover 15 along the means 12 to afford access to the interior of the container. The filter 10 will have substantially the shape of the opening of the nostril, i.e., tapered at the ends and arcuate, with one end being larger then the other. In the preferred embodiment, the filter will contain a quantity substantially liquid or jelled material such as a medicament, light oil to trap pollutants or the like. The filter 10 per se, will also preferably be encased in a flexible yet shape retaining non-allergenic, porous container 14 that has substantially the same shape as the filter 10 yet is slightly larger. The container 14 will be preferably open on at least one side to facilitate insertion of the filter element 13 therein when cover 15 is slid away from the opening formed by the open side, being the side that faces inward toward the outlet of the nostril. The cover 15 having an aperature 16 receive the means 12 so that cover 15 can slide towards each other on the means 12 to replace the filter element 13. The end 11 preventing the container 14 from becoming disengaged from the means 12 by providing a relatively large area of contact to secure end 11 to the interior of the wall of container 14.

Since it is obvious that numerous changes and modifications can be made in the above-described details without departing from the spirit and nature of the invention, it is understood that all such changes and modifictions are included within the scope of the invention.

What is claimed is:

1. A nasal filter device adapted to be inserted into the nostrils of the nose, comprising a pair of walled containers each having an open side and an opposite perforated side, each open side facing toward the other open side, flexible bridge means having distal end portions extending through said respective open sides and disposed in respective said containers and fixed thereto, a pair of perforated covers complementally configured to span respective open sides of said containers, each said cover having an aperture, said flexible bridge means extending through said apertures, said covers operative to move towards each other on said bridge means, and porous filter means removably disposed in said containers, said containers having substantially the shape of said nostrils.

2. The device as claimed in claim 1 wherein said means is a non-allergenic flexible, shape retaining material.

3. The device as claimed in claim 1 where said container is a non-allergenic shape retaining flexible member.

4. The device as defined in claim 1 where in said filter is adapted to be inserted into the nasal passage.

5. The device as defined in claim 1 wherein said flexible bridge means is adapted to be disposed beneath the septum.

* * * * *